United States Patent
Chon et al.

(10) Patent No.: US 10,653,362 B2
(45) Date of Patent: May 19, 2020

(54) MOTION AND NOISE ARTIFACT DETECTION AND RECONSTRUCTION ALGORITHMS FOR PHOTOPLETHYSMOGRAM AND EQUIVALENT SIGNALS

(71) Applicant: WORCESTER POLYTECHNIC INSTITUTE, Worcester, MA (US)

(72) Inventors: Ki H. Chon, Worcester, MA (US); Jo Woon Chong, Worcester, MA (US); Duy Dao, Malden, MA (US); Hamed Salehizadeh, Worcester, MA (US)

(73) Assignee: Wavefront Research Inc., Northampton, PA (US)

( * ) Notice: Subject to any disclaimer, the term of this patent is extended or adjusted under 35 U.S.C. 154(b) by 669 days.

(21) Appl. No.: 15/010,345

(22) Filed: Jan. 29, 2016

(65) Prior Publication Data
US 2016/0220188 A1     Aug. 4, 2016

Related U.S. Application Data

(60) Provisional application No. 62/109,183, filed on Jan. 29, 2015.

(51) Int. Cl.
*A61B 5/02*     (2006.01)
*A61B 5/00*     (2006.01)
(Continued)

(52) U.S. Cl.
CPC ........ *A61B 5/7207* (2013.01); *A61B 5/02416* (2013.01); *A61B 5/1455* (2013.01);
(Continued)

(58) Field of Classification Search
CPC ... A61B 5/7207; A61B 5/1455; A61B 5/7267; A61B 5/725; A61B 5/7257; A61B 5/02416
See application file for complete search history.

(56) References Cited

U.S. PATENT DOCUMENTS 5,853,364 A * 12/1998 Baker, Jr. ........... A61B 5/02416
                                                           600/300
2008/0167564 A1 * 7/2008 Hete .................. A61B 5/02405
                                                           600/508

(Continued)

FOREIGN PATENT DOCUMENTS

WO       1998042250 A1    2/2000
WO   WO-2013043157 A2 *  3/2013  ........... A61B 5/7203

OTHER PUBLICATIONS

Couceiro, Ricardo, et al. "Detection of motion artifacts in photoplethysmographic signals based on time and period domain analysis." 2012 Annual International Conference of the IEEE Engineering in Medicine and Biology Society. IEEE, 2012. (Year: 2012).*

(Continued)

*Primary Examiner* — Navin Natnithithadha
*Assistant Examiner* — Andrey Shostak
(74) *Attorney, Agent, or Firm* — Culhane Meadows; Orlando Lopez

(57) ABSTRACT

A pulse oximeter embedded with a motion and noise artifact (MNA) detection algorithm based on extraction of time-varying spectral features that are unique to the clean and corrupted components.

20 Claims, 10 Drawing Sheets

(51) Int. Cl.
  *A61B 5/024*   (2006.01)
  *A61B 5/1455*  (2006.01)
(52) U.S. Cl.
  CPC ............ *A61B 5/725* (2013.01); *A61B 5/7257* (2013.01); *A61B 5/7267* (2013.01)

(56) References Cited

U.S. PATENT DOCUMENTS

2008/0287815 A1* 11/2008 Chon ................... A61B 5/0806
                                                    600/507
2011/0077484 A1*  3/2011 Van Slyke ......... A61B 5/02416
                                                    600/324
2016/0270733 A1*  9/2016 Hansson .............. A61B 5/0215

OTHER PUBLICATIONS

Couceiro, R. et al., "Detection of motion artifacts in photoplethysmographic signals based on time and period domain analysis", The Effect of Appli ed Compressive Loading on Tissue-Engi Neered Cartilage Constructs Cultured With TGF-BETA3, IEEE, Aug. 28, 2012 (Aug. 28, 2012), pp. 2603-2606.
Salehizadeh, S. et al., "A Novel Time-Varying Spectral Filtering Algorithm for Reconstruction of Motion Artifact Corrupted Heart Rate Signals During Intense Physical Activities Using a Wearable Photoplethysmogram Sensor", Sensors, vol. 16, No. 1, Dec. 23, 2015 (Dec. 23, 2015), p. 10.
The International Search Report and The Written Opinion for PCT/US16/15650 dated May 17, 2016.

* cited by examiner

MOTION AND NOISE ARTIFACT DETECTION AND RECONSTRUCTION ALGORITHMS FOR PHOTOPLETHYSMOGRAM AND EQUIVALENT SIGNALS

CROSS REFERENCE TO RELATED APPLICATIONS

This application claims priority to and benefit of U.S. Provisional Application No. 62/109,183, filed Jan. 29, 2015, entitled MOTION AND NOISE ARTIFACT DETECTION AND RECONSTRUCTION ALGORITHMS FOR PHOTOPLETHYSMOGRAM SIGNALS, the contents of which are incorporated by reference herein in their entirety for all purposes.

STATEMENT REGARDING FEDERALLY SPONSORED RESEARCH OR DEVELOPMENT

This invention was made with U.S. Government support from the United States Army Medical Research and Material Command under Grant No. W81XWH-12-1-0541. The U.S. Government has certain rights in the invention.

BACKGROUND

These teachings relate generally to pulse oximeters and, more specifically, to pulse oximeters with algorithms embedded for real-time detection of motion and noise artifacts.

A pulse oximeter (PO) is a non-invasive, low cost device that is widely used in hospitals and clinics to monitor heart rate (HR) and arterial oxygen saturation (SpO2). Recently, there have been efforts to derive other physiological parameters from Photoplethysmogram (PPG), as recorded by a PO. The fluctuations observed in a PPG are influenced by arterial, and venous blood, as well as autonomic and respiratory systems of the peripheral circulation. Such information could be used to more comprehensively phenotype cardiovascular health. Due to increasing health care costs, a single sensor from which multiple clinical datapoints can be derived such as a PO is very attractive from a financial perspective. Moreover, utilizing a PO as a multipurpose vital sign monitor has a clinical appeal, since the device is widely accepted by clinicians and patients because of its ease of use, comfort and accuracy in providing reliable vital signs. Knowledge of respiratory rate and HR patterns would provide useful clinical information in many situations where a PO is the sole available monitor. However, extraction of the above mentioned vital signs and other physiological parameters using PO is predicated on artifact-free PPG data. It is well known that the PPG is highly sensitive to artifacts, particularly those generated while the patient is in motion. This imposes a huge limitation on the usability of the PPG for ambulatory monitoring applications. Motion and noise artifacts (MNA) distorting PPG recordings can cause erroneous estimation of HR and SpO2. Although the intelligent design of sensor attachment, form factors and packaging can help to reduce the impact of motion disturbances by making sure that the sensor is securely mounted, they are not sufficient for complete MNA removal. Combating MNA in PPG has been the core focus of research for many years.

Although there are techniques which have been proposed to alleviate the effects of MNA, solutions to this problem still remain unsatisfactory in practice. Several algorithm-based MNA reduction methods have been proposed, such as time and frequency domain filtering, power spectrum analysis, and blind source separation techniques. These techniques reconstruct noise contaminated PPG such that a noise-reduced signal is obtained. However, the reconstructed signal typically contains incomplete dynamic features of the uncorrupted PPG signal and some algorithms are solely designed to capture only the HR and SpO2 information instead of the signal's morphology and its amplitudes, which are needed for other physiological derivations. Moreover, these reconstruction algorithms operate even on clean PPG portions where MNA reduction is not needed. This introduces unnecessary computation burden and distorts the signal integrity of the clean portion of the data. Hence, an accurate MNA detection algorithm, which identifies clean PPG recordings from corrupted portions, is essential for the subsequent MNA reduction algorithm so that it does not distort the non-corrupted data segments.

MNA detection methods are mostly based on a signal quality index (SQI) which quantifies the severity of the artifacts. Some approaches quantify the SQI using waveform morphologies or filtered output, while other derive the SQI with the help of additional hardware such as accelerometer and electrocardiogram. Statistical measures, such as skewness, kurtosis, Shannon entropy, and Renyi's entropy, have been shown to be helpful in determining the SQI. These statistical algorithms differentiate the distribution of amplitudes between PPG segments with an assumption that clean and corrupt segments would form two separate groups. However, PPG waveforms vary among patients, thus yielding multitude of amplitude distributions. Therefore, it would be difficult to obtain high accuracy from these algorithms in practice. A recently published MNA detection method uses time-domain features such as variability in heart rate, amplitude, and waveform morphology with the help of the support vector machine (SVM) classifier for detection. The algorithm, which was termed time-domain variability SVM (TDV-SVM) is shown to be more robust than other statistical-based algorithms as it uses successive difference and variability measures. However, this method is highly dependent on accuracy of the peak amplitude detection. Unlike the electrocardiogram (ECG), the PPG waveform does not have distinctive peaks which make accurate peak detection challenging. The dependency on a peak detection subroutine is a drawback of the TDV-SVM algorithm and inevitably affects its performance. Time-frequency (TF) techniques such as Smoothed Pseudo Wigner-Ville, Short Time Fourier Transform, Continuous Wavelet Transform, Hilbert-Huang Transform, and Variable Frequency Complex Demodulation (VFCDM) received considerable attention as means to analysis the signal of interest in both temporal and spectral domains.

While PPG signals are obtained from a pulse oximeter, other devices can produce signals that behave like PPG signals. For example, color video images obtained from handheld mobile devices (such as smartphones) behave as reflection PPG images There is therefore a need to provide a pulse oximeter with real-time detection of MNA to mitigate false readings of heart rates and oxygen saturation values during body movements, which can lead to a wider use of pulse oximeter device for ambulatory applications.

There is therefore also a need there is, therefore, to provide a device that uses signals that behave as PPG signals, where the device has a component for real-time detection of MNA to mitigate false readings of heart rates and oxygen saturation values during body movements, which can lead to a wider use of the device for ambulatory applications.

BRIEF SUMMARY

Disclosed herein are methods that can be embedded, in a pulse oximeter or a device that provides signals equivalent to PPG signals, for real-time detection of MNA to mitigate false readings of heart rates and oxygen saturation values during body movements.

In one or more embodiments, the method of these teachings for detection of motion and noise artifacts in a Photoplethysmogram (PPG) or equivalent signal includes obtaining a time frequency spectrum of a segment of the PPG or equivalent signal, obtaining, from the time frequency spectrum, a noise quality index for the segment and applying a statistical learning method to determine whether the segment is corrupted by motion and noise artifacts or not corrupted by motion and noise artifacts.

In one instance, the statistical learning methods includes using a Support Vector Machine (SVM).

In one or more embodiments, the system of these teachings for detection of motion and noise artifacts in a Photoplethysmogram (PPG) or equivalent signal includes a processor configured to obtain a time frequency spectrum of a segment of the PPG or equivalent signal, obtain, from the time frequency spectrum, a noise quality index for the segment and apply a statistical learning method to determine whether the segment is corrupted by motion and noise artifacts or not corrupted by motion and noise artifacts.

A number of other embodiments are disclosed herein below.

For a better understanding of the present teachings, together with other and further needs thereof, reference is made to the accompanying drawings and detailed description.

DETAILED DESCRIPTION

Figure 1A:
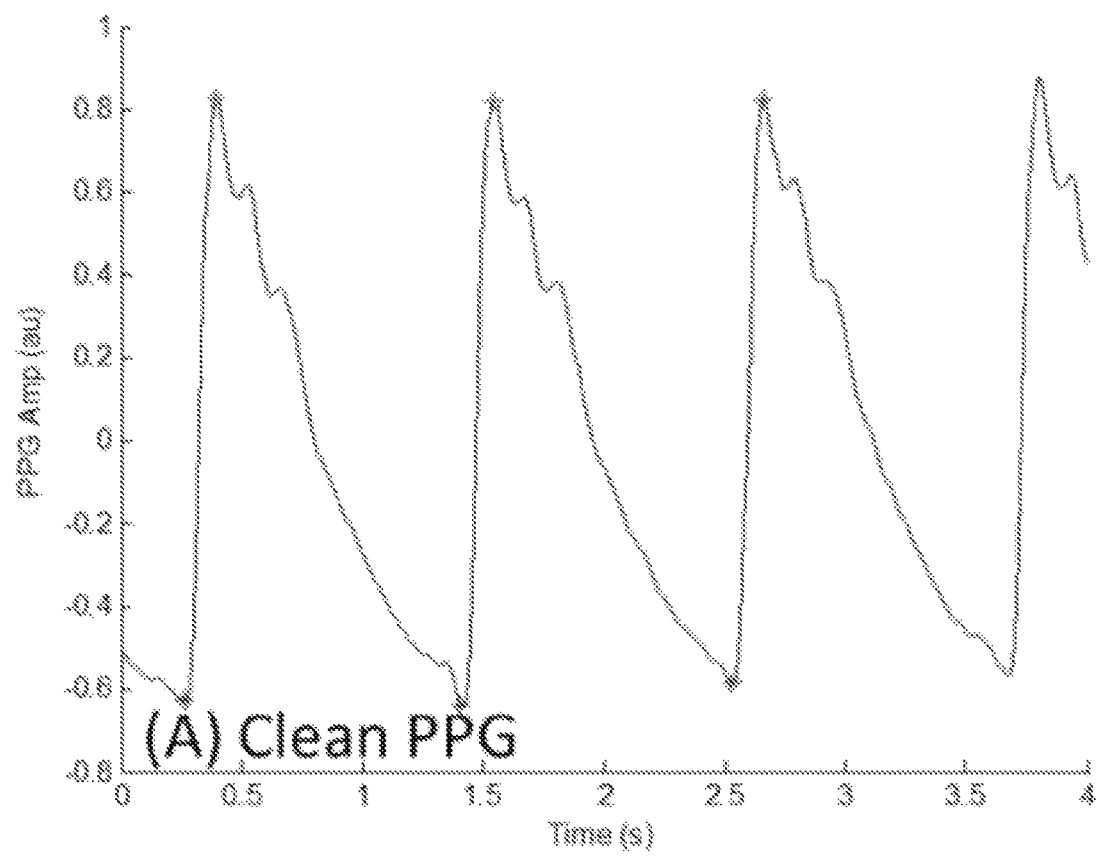
FIGS. 1A-D are graphs of the VFCDM-TFS of the present approach.
Figure 1B:
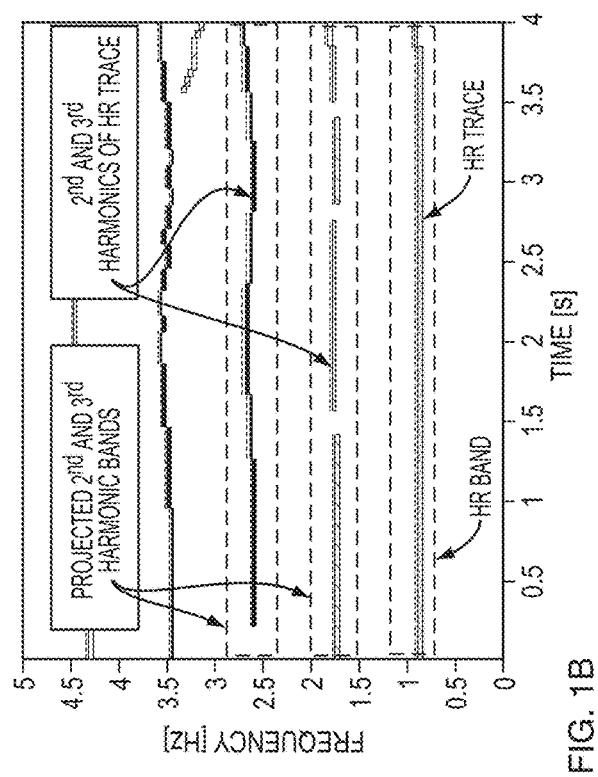
Figure 1D:
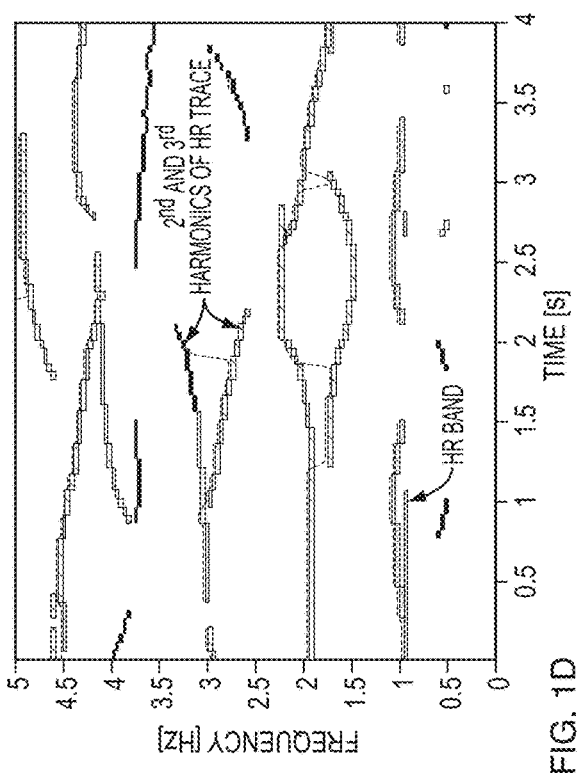
Figure 1C:
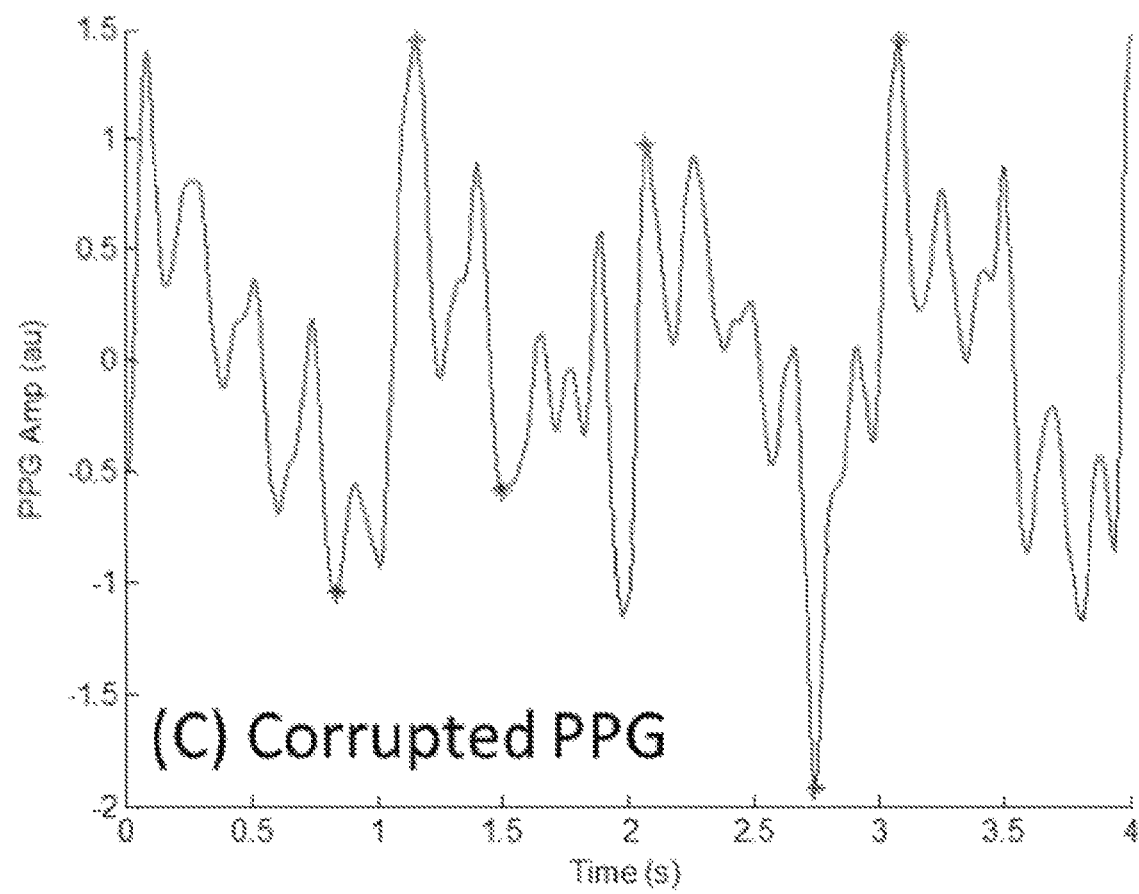

The following detailed description presents the currently contemplated modes of carrying out the disclosure. The description is not to be taken in a limiting sense, but is made merely for the purpose of illustrating the general principles of the disclosure.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

The following definitions are provided herein in order to facilitate elucidation of these teachings.

"Photoplethysmogram (PPG) or equivalent signal," as used herein, refers to signals obtained from a pulse oximeter or other devices that produce signals that behave like PPG signals obtained from the puke oximeter. A "physiological indicator signal," as used herein, refers to a signal that can be used to obtain measurements of one or more physiological parameters. Examples of physiological indicator signals, these teachings not being limited only to those examples, including photoplethysmograph (PPG) signals, and color images obtained from a portion of a subject's body (for example, but not limited to, obtained using the camera in a mobile communication device), which behave as refection PPG images. The one or more physiological parameters include heart rate and heart rate variability, respiratory rate, a measure of oxygen saturation, a measure of blood loss, and a measure of atrial fibrillation.

In one or more embodiments, the method of these teachings for detection of motion and noise artifacts in a Photoplethysmogram (PPG) or equivalent signal includes obtaining a time frequency spectrum of a segment of the PPG or equivalent signal, obtaining, from the time frequency spectrum, a noise quality index for the segment and applying a statistical learning method to determine whether the segment is corrupted by motion and noise artifacts or not corrupted by motion and noise artifacts. In one or more embodiments, the method of these teachings for physiological parameter monitoring includes detecting effects of motion artifacts in the measurements of the one or more physiological parameters and deciding whether to retain the measurements. In detecting effects of motion artifacts in the measurements of the one or more physiological parameters and deciding whether to retain the measurements, if noise/motion artifacts are not present, the segment is included in calculations of quantities of interest.

In one instance, obtaining the noise quality index includes determining a dominant frequency in the time frequency spectrum of the segment and normalizing the time frequency spectrum to the total power in a narrow band centered at the dominant frequency.

In one embodiment, the method of these teachings also includes determining a first trace of amplitudes in a narrow band spectrum of the time frequency spectrum centered at the dominant frequency, determining a second trace of amplitudes in a narrow band spectrum of the time frequency spectrum centered at twice the dominant frequency, determining a third trace of amplitudes in a narrow band spectrum of the time frequency spectrum centered at three times the dominant frequency, subtracting the first, second and third traces of amplitudes from the time frequency spectrum and obtaining, after subtracting, a total power remaining in the time frequency spectrum; the total power remaining hereinafter referred to as a residual noise power.

In another embodiment, the method of these teachings also includes determining a difference in frequency between the first trace and the second and third traces; the difference in frequency referred to as the projected difference.

In yet another embodiment, the method of these teachings also includes determining a difference between the dominant frequency and a heart rate obtained from peak to peak intervals from the PPG or equivalent signal in the time domain; the difference between the dominant frequency and the heart rate obtained from peak to peak intervals hereinafter referred to as a heart rate frequency difference.

In one instance, the noise quality index is a weighted sum of the residual noise power, the projected difference and the heart rate frequency difference; weights being selected such that each weighted factor represents less than a predetermined percentage of power in an uncorrupted segment. Embodiments in which one or two of the weights are zero are also within the scope of these teachings.

In one or more instances, and in the exemplary embodiment presented below, the statistical learning method is a Support Vector Machine (SVM). It should be noted that other statistical learning methods are also within the scope of these teachings.

In one or more embodiments, the system of these teachings for detection of motion and noise artifacts in a Photoplethysmogram (PPG) or equivalent signal includes a processor configured to obtain a time frequency spectrum of a segment of the PPG or equivalent signal, obtain, from the time frequency spectrum, a noise quality index for the segment and apply a statistical learning method to determine whether the segment is corrupted by motion and noise artifacts or not corrupted by motion and noise artifacts.

In other embodiments of the system of these teachings, the processor is configured to perform the method of these teachings.

In one or more embodiments, the computer program product of these teachings includes tangible (also referred to as non-transitory) computer usable media having computer readable code embodied there in which, when executed by one or more processors, causes the one or more processors to perform the method of these teachings.

In order to further elucidate these teachings, an exemplary embodiment is presented herein below. It should be noted that these teachings are not limited only to the exemplary embodiment.

EXAMPLE 1

Experimental Protocol and Preprocessing

PPG data were collected from healthy subjects in lab-controlled environment and also from patients enrolled in an emergency room. For the laboratory-controlled environment, both forehead and finger worn PO sensor data were collected from healthy subjects to have more control over the duration of MNA generated data to ensure that the detection algorithms were tested on a wide range of MNA durations. Data from participants recruited from the emergency room environment provided more realistic information about MNA in practice since participants in the lab-controlled study were allowed to move freely as long as the sensors were positioned properly. PPG data were collected by custom-made reflectance-type forehead and a transmission-type finger POs.

In laboratory-controlled head and finger movement data, motion artifacts were induced by head and finger movements for specific time intervals in both horizontal and vertical directions. For head movement data, 11 healthy volunteers were asked to wear the PO on the forehead along with a reference MASIMO Radical (MASIMO SET®) finger type transmittance pulse oximeter. After baseline recording for 5 minutes without any movement, subjects were instructed to introduce motion artifacts for specific time intervals varying from 10 to 50% within a 1 minute segment. For example, if a subject was instructed to perform left-right random movements for 6 seconds, 1 min segment of data would contain 10% noise. The finger laboratory movement data were recorded in a similar setup as the head data using a custom-made PPG finger sensor.

The patient PPG data were recorded from 10 subjects admitted to emergence rooms. Similar to the laboratory-controlled dataset, each patient was fitted with custom-made sensors (both forehead and finger) and the MASIMO POs on the forehead and fingers, respectively. The patients were admitted due to pain related symptoms and were not restrained from movements. Therefore, they were expected to generate different MNA characteristics in the recorded PPG.

To further evaluate the robustness of the present algorithm, Gaussian white-noise of 5 minute duration was added to the clean forehead and finger PPG data with varying signal-to-noise ratios (SNR) ranging from 40 dB to −5 dB. All PPG data were pre-processed by a $6^{th}$ order infinite impulse response (IIR) band pass filter with cut-off frequencies of 0.1 Hz and 10 Hz. (Other bandpass filters are within the scope of these teachings) Zero-phase forward and reverse filtering was applied to account for the non-linear phase of the IIR filter. Human visual inspection was also used to establish a MNA reference for the datasets. Three inspectors individually marked MNA corrupted portions of the PPG data. Disagreements of the marked portions were resolved by majority votes.

VFCDM Features from PPG Signals

VFCDM is a method for estimating time-frequency spectrum (TFS) of a time-varying signal (see, for example, Wang H, Siu K, Ju K, Chon K H. A high resolution approach to estimating time-frequency spectra and their amplitudes. Ann Biomed Eng. 2006 February; 34(2):326-38, which is incorporated by reference herein in its entirety and for all purposes). This method was shown to provide concomitant high time and frequency resolution as well as preservation of the amplitude distribution of the signal. VFCDM has two phases: (1) constructing an initial TFS (iTFS) using a method termed fixed frequency complex modulation (FFCDM); (2) the centered frequencies of the iTFS are used for further complex demodulation (CDM) to obtain even more accurate TFS and amplitude of the TFS. The VFCDM methodology is detailed as followed.

VFCDM

Consider a sinusoidal signal x(t) to be a narrow band oscillation with a time-varying center frequency $f(\tau)$, instantaneous amplitude $A(t)$, phase $\phi(t)$, and the direct current component $dc(t)$:

$$x(t)=dc(t)+A(t)\cos(\int_0^t 2\pi f(\tau)d\tau+\phi(t)) \quad (1)$$

For a given center frequency, the instantaneous amplitude information $A(t)$ and phase information $\phi(t)$ can be extracted by multiplying (3) by $e^{-j\int_0^t 2\pi f(\tau)d\tau}$ which results in the following:

$$z(t) = x(t)e^{-j\int_0^t 2\pi f(\tau)d\tau} \quad (2)$$

$$= dc(t)e^{-j\int_0^t 2\pi f(\tau)d\tau} + \frac{A(t)}{2}e^{j\phi(t)} +$$

$$\frac{A(t)}{2}e^{-j(\int_0^t 2\pi f(\tau)d\tau+\phi(t))}$$

From (2), if z(t) is filtered with an ideal low-pass filter (LPF) with a cutoff frequency $f_c<f_0$, then the filtered signal $z_{lp}(t)$ will contain only the component of interest:

$$z_{lp}(t) = \frac{A(t)}{2} e^{j\phi(t)} \quad (3)$$

The instantaneous frequency is given by $$f(t) = f_0 + \frac{1}{2\pi} \frac{d\phi(t)}{dt}$$

where $f_0$ is the centered frequency of interest. By changing the centered frequency followed by using the variable frequency approach as well as the LPF, the signal, x(t), will be decomposed into the sinusoid modulation by the CDM technique as follows:

$$x(t) = \sum_i d_i \quad (4)$$
$$= dc(t) + \Sigma_i A_i(t) \cos\left(\int_0^t 2\pi f_i(\tau) d\tau + \phi_i(t)\right)$$

The instantaneous frequency and amplitude of $d_i$ can be calculated using the Hilbert transform $$A(t) = 2|z_{lp}(t)| = [X^2(t) + Y^2(t)]^{1/2} \quad (5A)$$
$$X(t) = \text{real}(z_{lp}(t))$$
$$Y(t) = \text{imag}(z_{lp}(t)) = H[X(t)] = \frac{1}{\pi} \int \frac{X(t')}{t-t'} dt'$$

$$\phi(t) = \arctan\left(\frac{\text{imag}(z_{lp}(t))}{\text{real}(z_{lp}(t))}\right) = \arctan\left(\frac{Y(t)}{X(t)}\right) \quad (5B)$$

FFCDM operates by performing CDM on fixed frequency $f_0$ within confined bandwidth and repeat it over entire frequency band. In order to obtain even higher resolution TFS, center frequencies in iTFS obtained from FFCDM were used for subsequent CDM with finer bandwidth.

MNA Discriminative Feature from VFCDM-TFS

An example of VFCDM-TFS is shown in FIGS. 1A-D. The HR trace and two of its harmonic traces are termed as $FM_1$, $FM_2$, $FM_3$, respectively, with the corresponding amplitudes $AM_1$, $AM_2$, $AM_3$. The algorithm first determines the dominant frequency in the PPG segment termed $f_{HR}$. The TFS of the data segment is normalized by the total power in the $f_{HR}$ band. It then extracts $AM_1$ from a narrow band spectrum of the TFS centered at the dominant frequency $AM_1 \in [f_{HR}-BW, f_{HR}+BW]$. In one instance, the bandwidth of the band, BW, is about 0.2 Hz (other values of the bandwidth are within the scope of these teachings). The maximal power in each time instance is taken to form $AM_1$ in the segment. Once located, $AM_1$ is removed from the TFS. Similarly, $AM_2 \in [2f_{HR}-BW, 2F_{HR}+BW]$ and $AM_3 \in [3f_{HR}-BW, 3f_{HR}+BW]$ are found and removed. From the extracted TFS, FMs and AMs, three features were derived to quantify the noise level between clean versus corrupted PPG segments.

Residual Noise Power ($P_{noise}$)

After extracting the first three dominant traces, remaining power in the TFS is considered the residual noise power $P_{noise}$ and is denoted as:

$$P_{noise} = P_{TFS} - \Sigma_{i=1}^3 \Sigma_j AM_{i,j} \quad (6)$$

where $P_{noise}$ is the total power in the TFS after extracting the first three dominant traces. In a clean PPG segment, the first three harmonics would be located within the predetermined narrow band. Thus extracting their power would effectively remove most of the spectral power from the TFS. The remaining noise power would be negligibly small. On the other hand, artifacts in the corrupted PPG segment produce spectral power at various frequency locations which are often not associated with the harmonics' frequency bands. Some of these spectral power would not be extracted which in turn yields high $P_{noise}$ level.

Projected Frequency Modulation Difference ($df_{FM}$)

Projected difference is defined as the difference in frequency between the fundamental HR trace and its harmonic traces and is computed as:

$$df_{FM} = \Sigma_{i=2}^3 \Sigma_j FM_{1,j} - i \times FM_{i,j} \quad (7)$$

Similar to the previous assumption, frequency location of the harmonic traces are expected to be proportional to that of the fundamental trace, which would result in a low $df_{FM}$ for a clean segment. For artifact corrupted segment, the proportionality in the frequency of the harmonics would no longer hold, thus driving $df_{FM}$ value to be high.

Heart Rate Frequency Difference ($df_{HR}$)

Heart rate frequency difference is defined as the difference between the fundamental frequency modulation $FM_1$ and HR computed from time-domain peak calculation and is computed as:

$$df_{HR} = FM_1 - \frac{1}{\Delta\text{peak}} \quad (8)$$

where $\Delta$peak (sec) is the HR computed from the peak-to-peak intervals within a PPG segment. In one instance, a median of the peak-to-peak intervals within a PPG segment is used as the HR computed from time-domain peak calculation.

The three features $P_{noise}$, $df_{FM}$, and $df_{HR}$ are combined into a weighted sum that represents noise quality index, noiseQI in a PPG segment.

$$\text{noise}QI = c_1 P_{noise} + c_2 df_{FM} + c_3 df_{HR} \quad (9)$$

where $c_i$ is the weight of each feature and is determined empirically such that each weighted feature contributes no more than 5% in the clean PPG segments (other predetermined percentages are also within the scope of these teachings). In the instance where the predetermined percentage is 5%, a typical MNA-free PPG segment should not have noiseQI greater than 0.15.

The noiseQI is very sensitive as noise dynamics contained in only 1 second duration in a 4-second data segment is classified as noise corrupted. This is because the noise region introduces many frequencies and spectral dynamics that are distinctively dissimilar than the clean signal. Hence, as noted above, $P_{noise}$, $df_{FM}$, $df_{HR}$, and consequently the noiseQI of the MNA corrupted segment will all be significantly larger and distinct from the clean signal's values.

SVM-Based Detection of Motion/Noise Artifacts

Feature Extraction from PPG

The preprocessed PPG was used to extract the noiseQI, as mentioned above. A sliding window of length $L_1=8$ second with 50% overlap was used to extract the raw PPG signal. The signal was band-pass filtered at 0.1-20 Hz and then down-sampled to 20 Hz. Only the middle portion of length $L_2=4$ second of the resulting TFS was considered for further processing. This is because, as shown below, the middle 4 second data length from the initial $L_1$=8 second for the subsequent VFCDM analysis provided the best accuracy in detection of MNA.

Figure 2A:
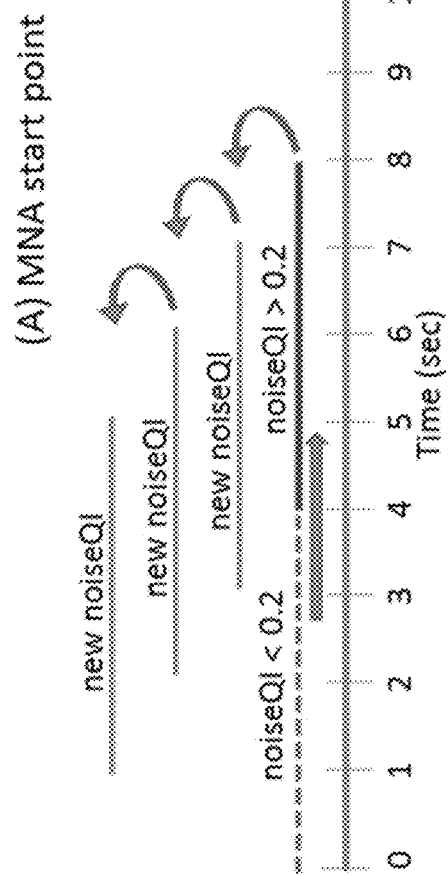
FIGS. 2A-B illustrate trace-back strategy to determine the start and end points of MNA.
Figure 2B:
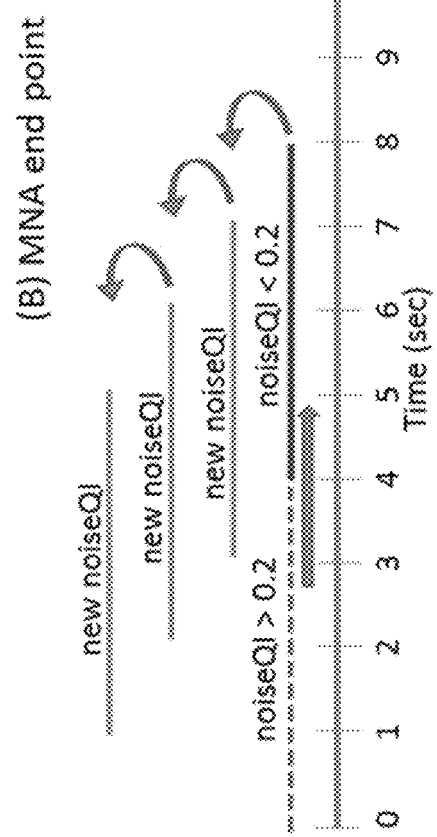
Figure 3:
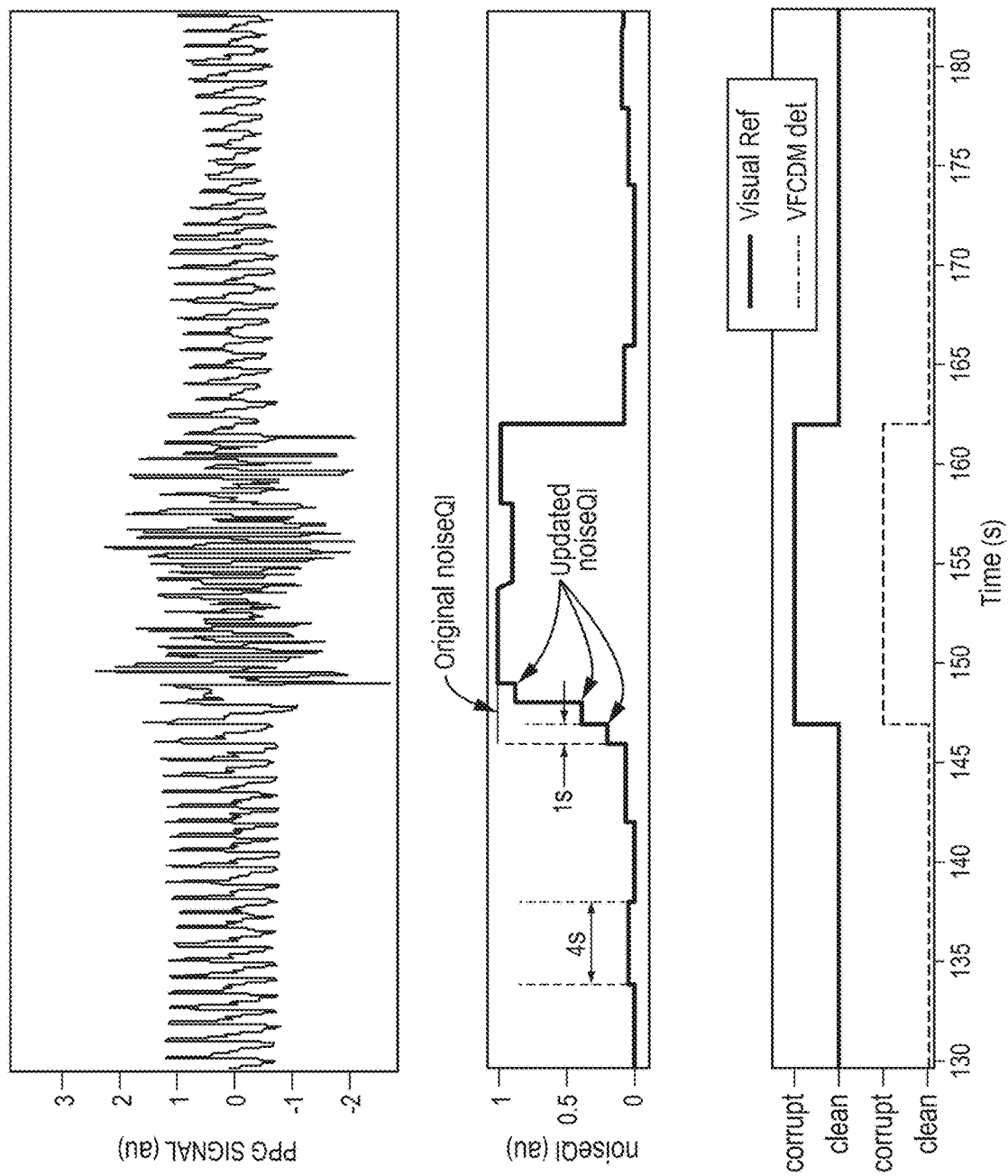
FIG. 3 illustrates examples of the trace-back mechanism.

To accurately pinpoint the time occurrence of MNA, a trace-back strategy was implemented, which is triggered when the noiseQI value changes its state as illustrated in FIGS. 2A-B. When noiseQI goes from lower than a threshold value of 0.2 to greater than 0.2 (it should be noted that others threshold values are within the scope of these teachings; for example, a threshold value of 0.15 would be within the scope of these teachings), the trace-back algorithm computes a new noiseQI three times with shifting backward a second at each time instant. For example, in FIG. 2A, noiseQI changes to a value that is greater than 0.2 at time duration 4-8 seconds. The trace-back scheme would call the VFCDM routine to compute new noiseQI values for the back-shifted segments at time durations starting at 3-7 seconds, 2-6 seconds, and ending at 1-5 seconds. The threshold noiseQI=0.2 was empirically determined to represent the presence of MNA. As detailed above, the VFCDM algorithm is designed to indicate that a segment is corrupted even if only 1 second of the 4 second duration data contain MNA. Hence, since the 3-7 second segment is determined to be corrupted, it allows deduction that the 8th second time point is corrupted. The same logic applies to the 2-6 and 1-5 second segments. If MNA starts at the 5th second, it is expected that the updated noiseQI values would be low prior to the 5th second while remain high for the segments after the 5th second. Similarly, MNA end point is determined by applying the trace-back algorithm when noiseQI goes from higher than 0.2 to lower than 0.2. An example of the track-back strategy on an actual PPG signal is illustrated in FIG. 3.

Classification by Support Vector Machine (SVM)

SVM was applied to build a decision boundary to classify the MNA segment from the clean PPG data. SVM is widely used for classification and regression analysis due to its accuracy and robustness to noise. The SVM consists of training and test phases as briefly described in the following sections (see, for example, CHRISTOPHER J. C. BURGES, A Tutorial on Support Vector Machines for Pattern Recognition, which is incorporated by reference herein in its entirety and for all purposes).

The SVM takes a priori determined classification parameter values of the clean and corrupted PPG segments as a training data set, finds the support vectors among the training data set which maximize the margin (or the distance) between different classes, and then builds a decision boundary. If the estimated decision is different from its known label, the decision is regarded as a training error. A soft-margin SVM can set the boundary even when the data sets are mixed and cannot be separated. In the soft-margin SVM algorithm, slack variables are introduced to minimize the training error while maximizing the margin. Soft-margin SVM uses the following equation to find the support vectors.

$$\text{Minimize } C \sum_{sv=1}^{N} \delta_{SV} + \frac{1}{2} \langle w_s, w_s \rangle, \quad (10)$$

Subject to $T_{sv}(\langle w_s, y_{sv} \rangle + b_s) \geq \delta_{sv}$ for $sv = 1, 2, \ldots, N$ and $\delta\_sv \geq 0$ where C is a regulation parameter, N is the number of vectors, $\delta_{sv}$ is the slack variable, $w_s$ is weight vector and $\langle \bullet, \bullet \rangle$ is the inner product operation. The $T_{sv}$ is the $sv^{th}$ target variable, $y_{sv}$ is the $sv^{th}$ input vector data, and $b_s$ is the bias. The SVM decision boundary $F_{sv}$ is derived as $$F_{sv} = \langle w_s *, y \rangle + b_s * = 0 \quad (11)$$

where $w_s*$ and $b_s*$ are weight factor and bias, respectively, obtained from Eq. (20) and y is the input point. By transforming the $y_{sv}$ and y terms to $y_{sv} \rightarrow \Phi(y_{sv})$ and $y \rightarrow \Phi(y)$, the non-linear SVM can be transformed to a linear SVM. For nonlinear SVM, Eq. (20) is modified as $$T_{sv}(\langle w_s, \Phi(y_{sv}) \rangle + b_s) \geq 1 \quad (12)$$

To facilitate the operation in nonlinear SVM, a kernel function $K_s(\bullet, \bullet)$, which is a dot-product in the transformed feature space is used as the following:

$$K_s(y_{sv}, y_{sv'}) = \langle \Phi(y_{sv}), \Phi(y_{sv'}) \rangle \quad (13)$$

where sv'=1,2, . . . , N. Once the training phase is completed, the optimal support vectors for training data are determined. These vectors are then used to classify the testing data so that the optimal solution of mutually exclusive boundaries can be determined.

Results

Figure 4A:
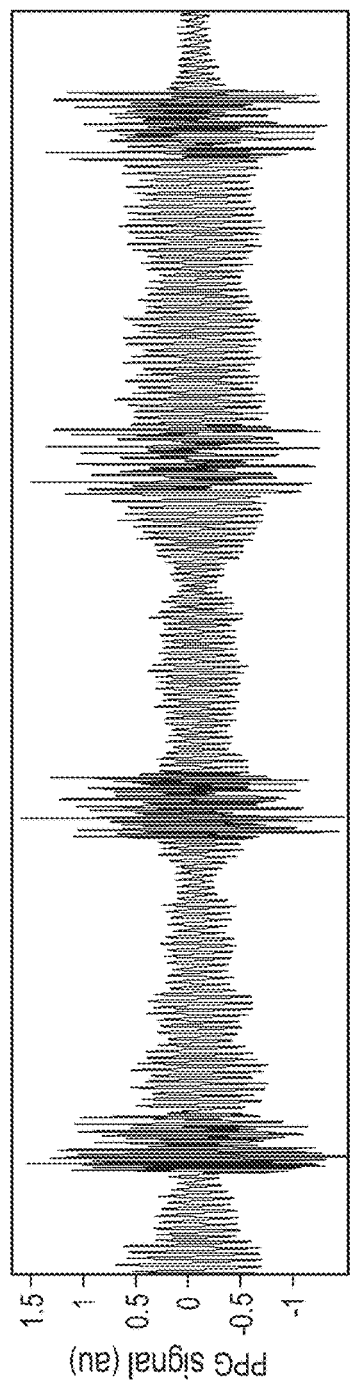
FIGS. 4A-C are examples of MNA detection using VFCDM.
Figure 4B:
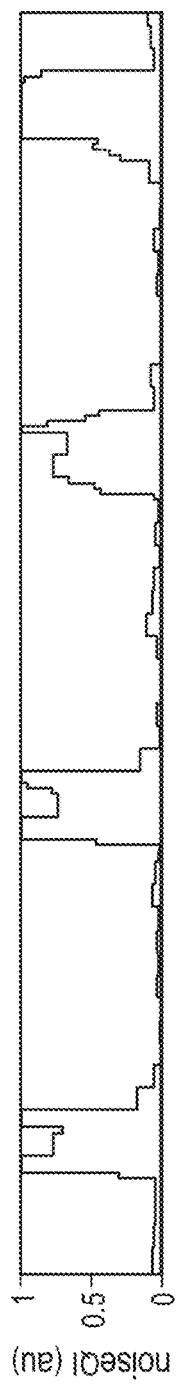
Figure 4C:
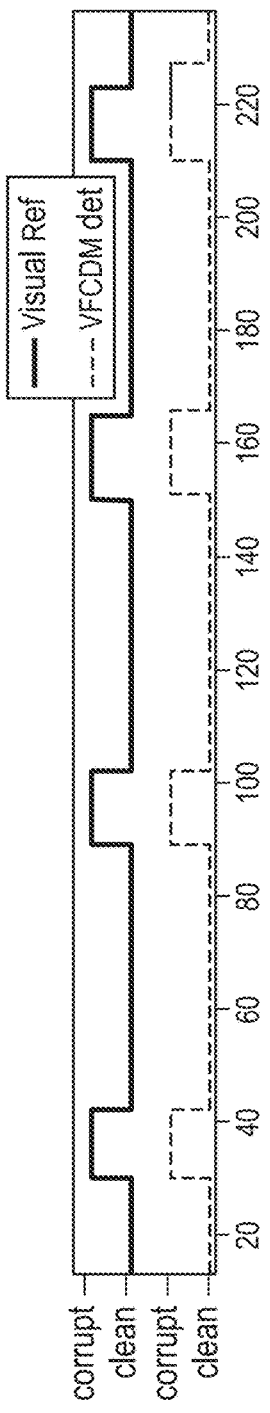

The performance of the VFCDM-based MNA detection algorithm was evaluated for various types (laboratory controlled, and hospital patients) of motion-corrupted PPGs to validate its performance for a wide range of scenarios. K-fold cross validation was adopted to evaluate the performance of the present algorithm. Specifically, for a dataset of N subjects, data from N−1 subjects were used for training and the unused subject data were used for testing. The train-test cycle was repeated N times, each time with a different test subject. The regularization parameter value C=10 was optimized for the linear kernel SVM by minimizing the training error. FIGS. 4A-C show representative illustrations of the performance of the present approach. FIG. 4A displays the filtered PPG signal containing both clean and MNA which is corrupted with varying levels of amplitude fluctuations. FIG. 4B depicts the corresponding noiseQI which was obtained according to Eq. (9). As shown, the noiseQI has low values for the clean portion of the data whereas it is high where the MNA occurs. The noiseQI is used for the SVM classifier to determine whether the given segment is clean or corrupted. FIG. 4C shows the classification results via the present approach along with the trained experts' decision of the occurrence of the MNA for comparison. For this example, it was observed that the present approach has a high sensitivity and specificity in detecting MNA.

The optimal window length was determined by varying $L_2$ from 3 to 6 sec while keeping $L_1$ constant at 8 sec. Detection performance was evaluated by comparing the classification results to the MNA reference (as determined visually by the experts) to yield accuracy, sensitivity, and specificity. Table I shows performance statistics in terms of accuracy (Acc), sensitivity (Sen), and specificity (Spe) of the present MNA detection algorithm at various window lengths ($L_2$) for the laboratory collected dataset. The window length of 4 sec ($L_2$=4 second) yielded the best performance in term of accuracy among the various window lengths examined.

TABLE I

MEAN ± STD. DEVIATION OF PERFORMANCE METRICS
OF THE PRESENT VFCDM USING VARIOUS WINDOW LENGTH

| | L | 3 s | 4 s | 5 s | 6 s |
|---|---|---|---|---|---|
| Lab. | Acc | 86.9 ± 5.5 | 96.9 ± 1.4 | 87.2 ± 4.2 | 84.1 ± 9.3 |
| Head | Sen | 81.8 ± 9.7 | 96.3 ± 2.4 | 80.3 ± 6.8 | 75.5 ± 16.4 |
| | Spe | 89.4 ± 6.2 | 97.7 ± 2.0 | 80.3 ± 3.1 | 89.3 ± 8.0 |

Figure 5:
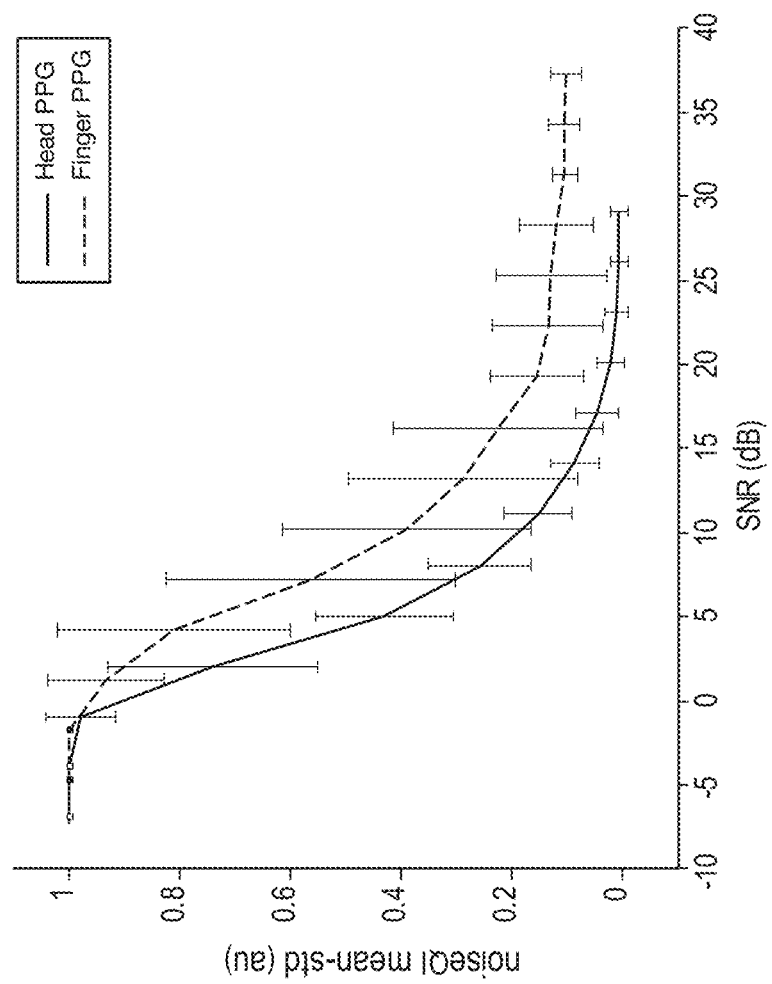
FIG. 5 is a graph of noise quality index (noiseQI) computed from the additive white-noise-corrupted PPG data at various signal-to-noise ratios (SNR)

The noiseQI value indicates the amount of noise present in the PPG segment. It is of interest to evaluate how well this parameter correlates with the actual noise at various levels. Therefore, the noiseQI values were computed for simulated data consisting of clean forehead and finger PPG data corrupted by additive white noise of varying SNR levels. The results are shown in FIG. 5. As shown, the noiseQI is consistently low for PPG signals with high SNR values and high for PPG signals with low SNR values with reaching a unity value for SNR less than 0 dB for both finger and forehead PPG data.

Figure 6:
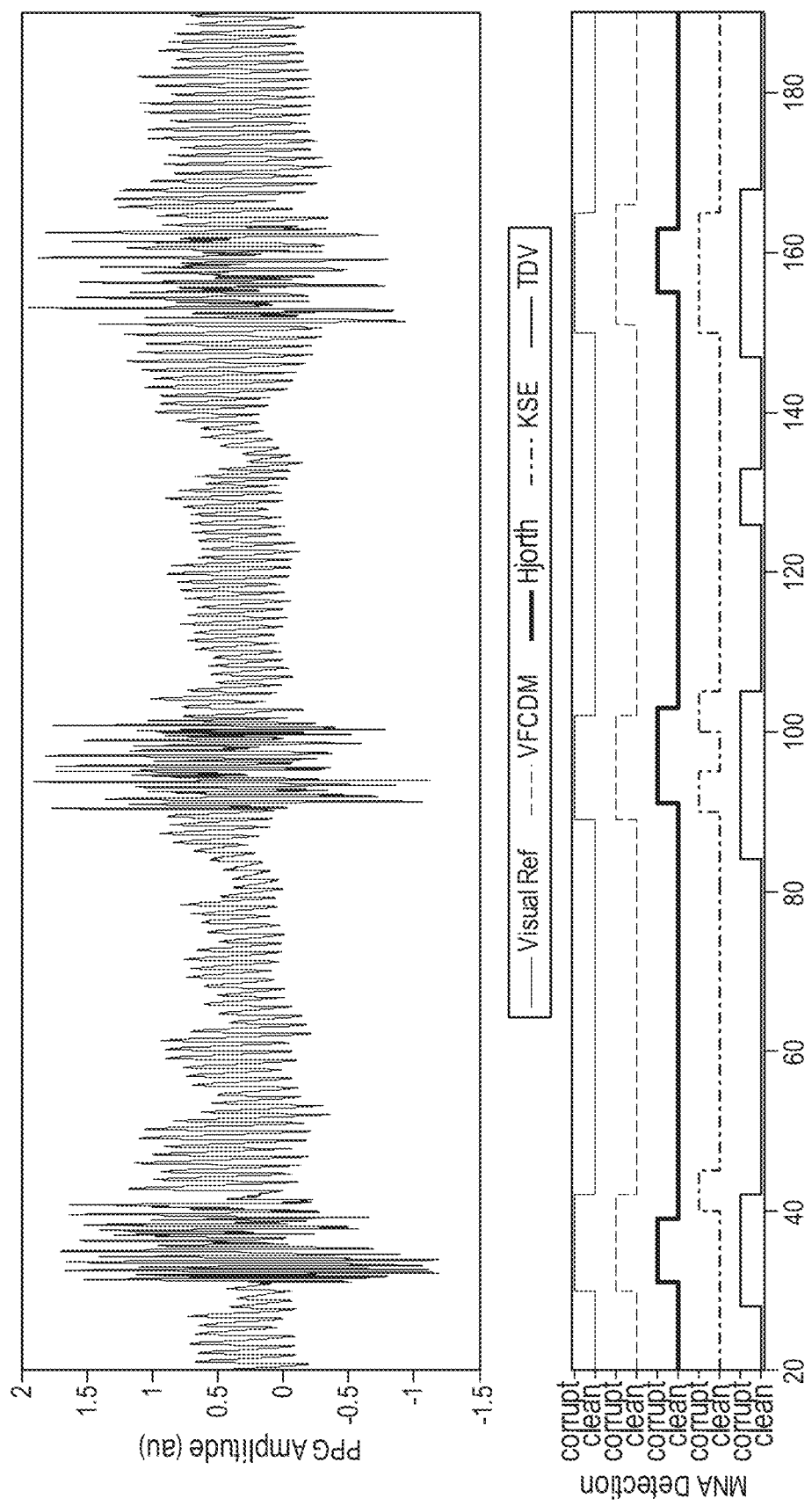
FIG. 6 is an example of MNA detection using the present VFCDM method versus other methods.

The present algorithm was compared with three other recently published MNA detection algorithms: 1) Hjorth features (Hjorth), 2) time-domain variability SVM (TDV-SVM) approach, and 3) Kurtosis-Shannon Entropy (KSE) features. A representative example of the MNA detection comparing all of the aforementioned methods is illustrated in FIG. 6. Performance results of each method are presented in Table II.

TABLE II

MEAN ± STD. DEVIATION OF PERFORMANCE
METRICS OF THE PRESENT VFCDM, OTHER METHODS

| | | VFCDM | Hjorth | TDV | KSE |
|---|---|---|---|---|---|
| Lab. | Acc | 96.9 ± 1.4 | 72.5 ± 10.7* | 93.4 ± 3.5* | 83.1 ± 7.3* |
| Head | Sen | 96.3 ± 2.4 | 47.2 ± 28.8* | 88.8 ± 7.9* | 56.6 ± 17.9* |
| | Spe | 97.7 ± 2.0 | 84.4 ± 4.6* | 96.7 ± 3.0 | 91.5 ± 1.1* |
| Unmass. | Acc | 95.5 ± 2.2 | 69.5 ± 21.8* | 89.8 ± 1.4* | 85.1 ± 8.3* |
| Head | Sen | 91.1 ± 3.5 | 53.8 ± 26.1* | 84.6 ± 2.9* | 68.7 ± 17.7* |
| | Spe | 96.3 ± 1.4 | 84.5 ± 8.8* | 94.3 ± 4.0 | 86.4 ± 7.8* |
| Lab. | Acc | 97.7 ± 1.4 | 91.1 ± 6.9* | 94.4 ± 3.3* | 58.5 ± 20.7* |
| Finger | Sen | 96.3 ± 2.6 | 83.5 ± 21.0* | 94.7 ± 3.4 | 34.6 ± 12.2* |
| | Spe | 98.2 ± 1.4 | 96.2 ± 3.0 | 94.7 ± 3.0* | 86.3 ± 15.7* |
| Unmass. | Acc | 95.5 ± 2.4 | 71.0 ± 19.0* | 89.6 ± 2.3* | 88.3 ± 2.7* |
| Finger | Sen | 89.2 ± 2.0 | 41.1 ± 27.6* | 85.2 ± 3.8* | 71.5 ± 8.8* |
| | Spe | 97.2 ± 2.1 | 88.4 ± 7.5* | 95.1 ± 0.8 | 93.6 ± 1.5* |

Figure 7A:
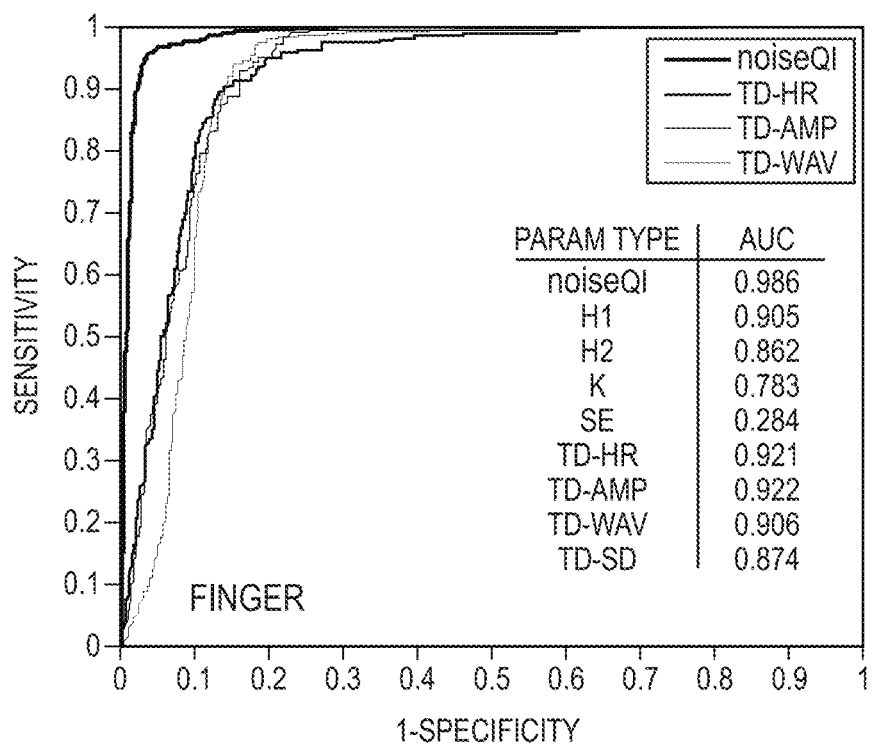
FIGS. 7A-B are graphs of receiver-operative-curves (ROCs) of all the features used in MNA detection algorithms.
Figure 7B:
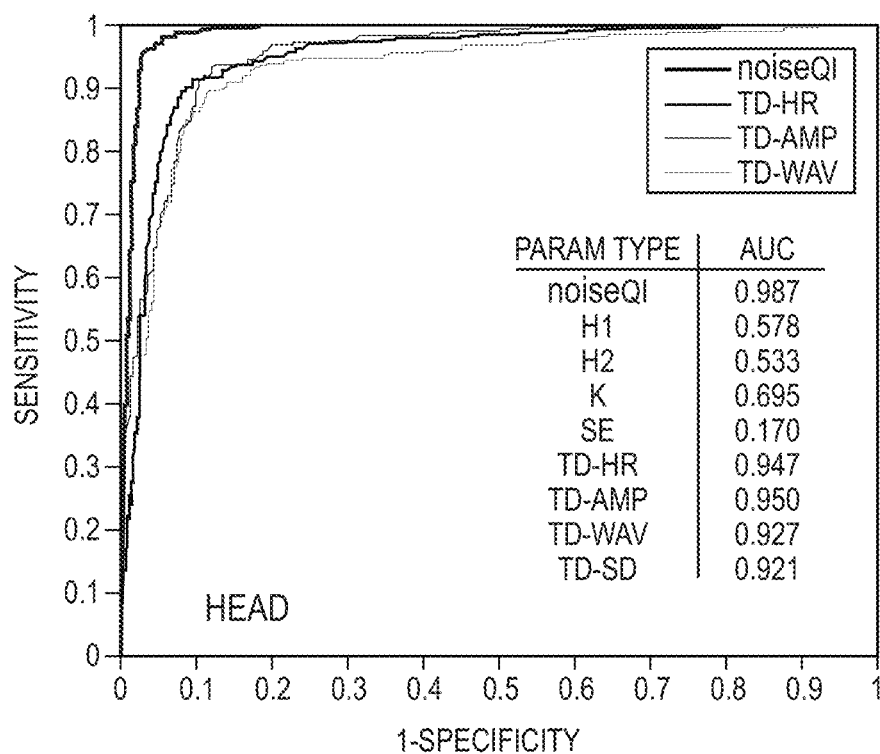

*indicate statistical significance (p < 0.01) between the present method versus the others Two-sample one-sided Welch's t-tests at 95% confidence interval was performed to assess the significance of the accuracy, sensitivity, and specificity results from the K-fold cross-validation. In order to measure and compare the detection powers, receiver operative characteristic (ROC) curves were generated for all the features used in the present VFCDM algorithm and other detection algorithms. Areas under these curves (AUCs) represent the strength of these features. In FIG. 7, ROC curves with highest AUC values were shown. The VFCDM-derived features obtained the highest AUC values among all methods compared.

In addition to accurate MNA detection, the other attractive feature of the present algorithm is that it is able to accurately locate the start and end points of MNA occurrences. Accurate detection of the start and end time of the MNA is important for the subsequent reconstruction of the MNA-corrupted data in order not to miss the MNA portion of data for reconstruction or avoid having to reconstruct the noisy portion of the PPG signal when the data segment is designated to be clean. To evaluate the algorithm's effectiveness in pinpointing the start and end time of the MNA, the time difference of start and end points was computed between the visual reference and detection algorithms' results. The time difference is termed detection transition time, DTT, which reflects how accurate on average the MNA algorithm detects the start and end time of the MNA. Table III provides DTT comparison of the VFCDM algorithm and other detection algorithms. As shown in Table III, the algorithm's detection accuracy of the duration of the MNA is significantly better than three other methods compared. The algorithm is off by less than 1 second whereas the second best algorithm, the Hjorth, is off by more than 2 seconds and the least accurate method, the KSE, is off by more than 4 seconds.

TABLE III

MEAN ± STD. DETECTION OF TRANSITION TIME,
DTT OF THE VFCDM METHOD AND OTHER METHODS.

| Algorithm | DTT (sec) |
|---|---|
| VFCDM | 0.94 ± 0.65 |
| Hjorth | 2.17 ± 0.37* |
| KSE | 4.24 ± 2.42* |
| TDV | 2.75 ± 0.96* |

*indicate statistical significance (p < 0.01) between the present method versus the others Discussion Disclosed is a pulse oximeter using a novel MNA detection method that uses dynamic characteristics of the corrupted PPG derived via the VFCDM. The efficacy of the detection method was validated using contrived motion data from healthy subjects and unconstrained MNA data from participants recruited from a hospital setting. In this study, several key features associated with MNA, derived from the VFCDM-based time-frequency spectrum, were utilized for detection of MNA. By transforming the PPG time series into the time-frequency domain, time-varying characteristics were better captured of the MNA. Specifically, it was recognized that PPG's clean signal dynamics are largely concentrated at the heart rate and its harmonic frequency bands. Hence, the presence of large amplitudes in the other frequency bands must be associated with MNA. This is clearly seen in FIG. 1B as VFCDM results from a clean PPG signal yields distinct peaks across all times at the HR frequencies and its two successive harmonic frequencies. Therefore, the TFS was divided into three narrow band spectra and tracked down these amplitude traces accordingly. In a clean PPG segment (shown in FIGS. 1A-B) most of the spectral power is concentrated in the $FM_1$, $FM_2$, and $FM_3$ traces since the signal is sinusoidal-like and periodic in nature. In a MNA corrupted PPG segment shown in FIGS. 1C-D, however, the signal is disturbed by inconsistent changes in the signal amplitude due to motion. These changes are typically irregular thus creating various spectral contents in the resulting TFS and eventually yielding high noiseQI values as defined in Eq. (8). Hence, the noiseQI values provide a quantitative measure of the MNA that is present in the PPG signal.

Results in FIG. 5 indicate that if the SNR cutoff threshold is set at 15 dB to discriminate between the clean and corrupted PPG data segments, then the corresponding noiseQI cutoff threshold would be around 0.14, and 0.22 for the head and finger data, respectively. Finger PPG waveforms for some people contain prominent traces of the dicrotic notch, which results in additional high frequency components. The VFCDM algorithm assumes that the HR cycle is the dominant component of the PPG waveform and the remaining components are considered as noise. Therefore, the noiseQI values of the finger PPG are higher than of the head PPG due to additional high frequency components introduced by the dicrotic notch. It can also be speculated that PPG recorded from peripheral regions (e.g., finger) is modulated at a higher intensity compared to forehead, which may explain the higher noiseQI values for the former location. Hence, due to the intrinsic difference in morphological properties of PPG recorded from the finger and forehead, training for MNA detection needs to be done separately for these two measurement locations.

The detection accuracy on both lab-controlled and UMMC datasets using the present methods outperformed the other three detection methods: Hjorth, TDV-SVM, and KSE. Each method's detectability was first compared based on their own unique feature selection by evaluating the area under the ROC curve. The AUCs showed that the noiseQI feature provided the highest value at 0.986 for both finger and forehead recorded PPG, as shown in FIG. 7. Concomitantly, the accuracy, sensitivity and specificity values of the present method were significantly higher than all other methods as indicated in Table II.

The eventual aim of the present algorithm is to detect MNA in real time. The algorithm only takes 33.3 ms to compute noiseQI for a 4s PPG window length using MATLAB® running on a PC with the INTEL®XEON® processor operating at 3.6 GHz. Therefore, it would be straightforward to optimize the algorithm for real time detection of MNA in a PPG signal.

In conclusion, the present approach is an accurate MNA detection algorithm that utilizes both time and spectral features to classify between a clean and corrupted PPG data segments. Comparison of the algorithm to existing methods using two datasets far better performance of the algorithm that other contemporary MNA detection algorithms. The algorithm also showed superiority with respect to detecting onset and offset of MNA. Moreover, the algorithm is real-time realizable and it is applicable to either transmission (finger) or reflectance (forehead) recorded PPG signals.

Figure 8:
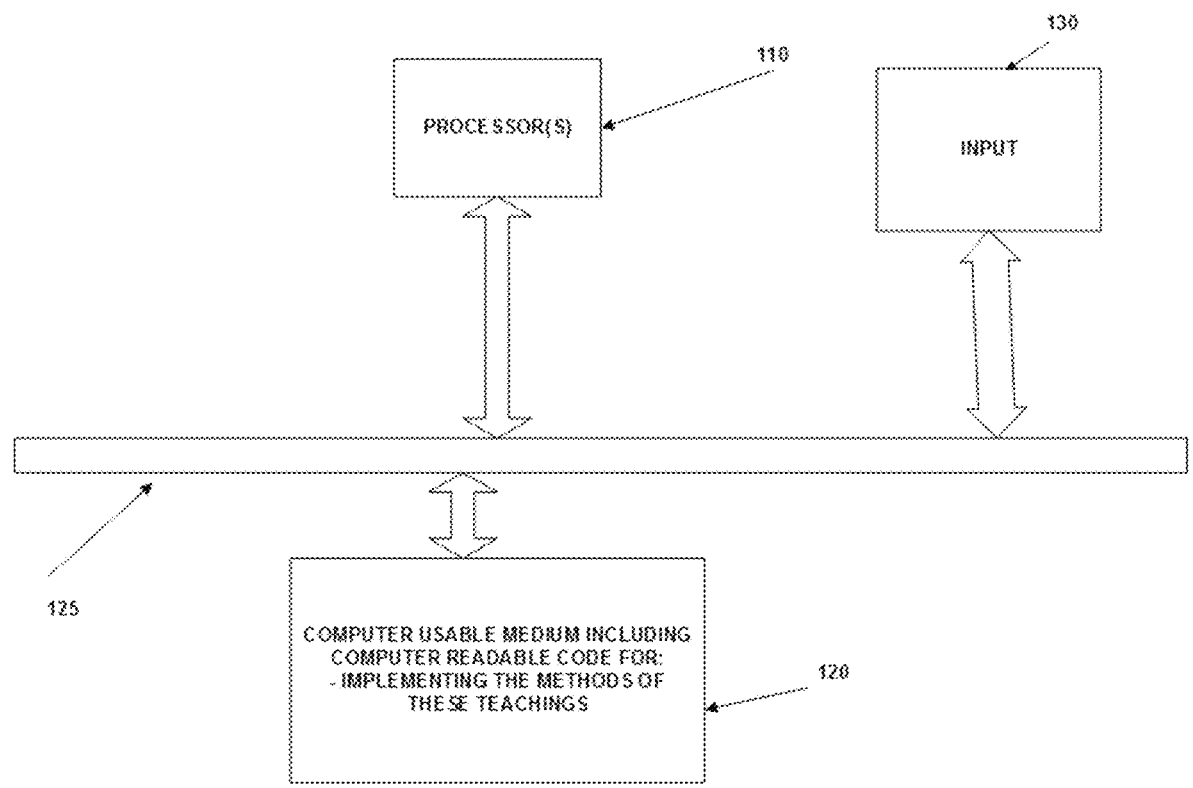
FIG. 8 is a schematic block diagram representation of one embodiment of the system of these teachings.

In one embodiment, the system of these teachings includes one or more processors and one or more computer usable media having computer readable code embodied therein, the computer readable code causing the one or more processors to execute the method of these teachings, shown in FIG. 8. Referring to FIG. 8, in the embodiment shown there in, one or more processors 110 are operatively connected to computer usable media 120 that has computer readable code embodied therein, which, when executed by the one or more processors 110, causes the one or more processors to perform the method of these teachings. An input device 130 is operatively connected to the one or more processors 110 and to the computer usable media 120 and enables the inputs of the PPG data segments. The one or more processors 110, the computer readable media 120 and the input device 130 are operatively connected by means of a computer connection component 125 (such as a computer bus).

The capability to extract accurate PPG equivalent signals, HR signals, heart rate variability dynamics, the respiratory rates and oxygen saturation information directly from the green, red, and blue band signals from a smart phone is detailed in a recently published paper (see also PCT Publication No. WO2012100175, corresponding to PCT/US2012/022049, PHYSIOLOGICAL PARAMETER MONITORING WITH A MOBILE COMMUNICATION DEVICE, filed on Jan. 20, 2012, and corresponding U.S. Published application 2012190947, PHYSIOLOGICAL PARAMETER MONITORING WITH A MOBILE COMMUNICATION DEVICE, which are incorporated by reference herein in their entirety and for all purposes).

The following is a disclosure by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metallization(s) interconnects of the base gate array ASIC architecture or selecting and providing metallization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD ROM, a DVD or a CD), or other type of memory system which maintains data even after power is removed from the system.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer to peer networks and the like. Different portions of the software program code/instructions and data can be obtained at different times and in different communication sessions or in a same communication session. The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instance of time.

In general, a tangible machine readable medium includes any tangible mechanism that provides (i.e., stores) information in a form accessible by a machine (i.e., a computing device, which may be included, e.g., in a communication device, a network device, a personal digital assistant, a mobile communication device, whether or not able to download and run applications from the communication network, such as the Internet, e.g., an I-phone, Blackberry, Droid or the like, a manufacturing tool, or any other device including a computing device, comprising one or more data processors, etc.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although these teachings have been described with respect to various embodiments, it should be realized these teachings are also capable of a wide variety of further and other embodiments within the spirit and scope of the appended claims.

What is claimed is:

1. A computer implemented method for physiological parameter monitoring using a signal used as a Photoplethysmogram (PPG) signal, the computer implemented method comprising:
    obtaining a time frequency spectrum of a segment of the signal used as the PPG signal;
    obtaining, from the time frequency spectrum, a noise quality index for the segment; the noise quality index being used to determine whether the segment is corrupted by motion and noise artifacts;
    wherein obtaining a noise quality index comprises:
        determining a dominant frequency in the time frequency spectrum of the segment;
        normalizing the time frequency spectrum to a total power in a narrow band centered at the dominant frequency;
        determining a first trace of amplitudes in the narrow band spectrum of the time frequency spectrum centered at the dominant frequency;
        determining a second trace of amplitudes in a narrow band spectrum of the time frequency spectrum centered at twice the dominant frequency;
        determining a third trace of amplitudes in a narrow band spectrum of the time frequency spectrum centered at three times the dominant frequency;
        subtracting the first, second and third traces of amplitudes from the time frequency spectrum;
        obtaining, after subtracting, a total power remaining in the time frequency spectrum, said total power remaining referred to as a residual noise power;
        determining a difference in frequency between the first trace and the second and third traces, the difference in frequency referred to as a projected difference;
    the noise quality index being a weighted sum of factors including the residual noise power and the projected difference; weights being selected such that each weighted factor represents less than a predetermined percentage of power in an uncorrupted segment;
    applying a statistical learning method, using the noise quality index, to determine whether the segment is corrupted by motion and noise artifacts or not corrupted by motion and noise artifacts;
and,
if motion and noise artifacts are not present, including the segment in determination of a physiological parameter.

2. The computer implemented method of claim 1 wherein the statistical learning method is a Support Vector Machine (SVM).

3. The computer implemented method of claim 1 further comprising determining a difference between the dominant frequency and a heart rate obtained from peak to peak intervals from the signal used as the PPG signal in a time domain, the difference between the dominant frequency and the heart rate obtained from peak to peak intervals referred to as a heart rate frequency difference; wherein the noise quality index also comprises the heart rate frequency difference; the noise quality index being a weighted sum of factors including the residual noise power, the projected difference and the heart rate frequency difference.

4. The computer implemented method of claim 3 wherein the statistical learning method is a Support Vector Machine (SVM).

5. The computer implemented method of claim 1 wherein the signal used as the PPG signal is preprocessed before obtaining the time frequency spectrum.

6. The computer implemented method of claim 5 wherein the signal used as the PPG signal is preprocessed by filtering with a bandpass filter of predetermined band width.

7. The computer implemented method of claim 1 wherein the time frequency spectrum is obtained using variable frequency complex demodulation.

8. A computer implemented method for physiological parameter monitoring using a signal used as a Photoplethysmogram (PPG) signal, the computer implemented method comprising:
obtaining a time frequency spectrum of a segment of the signal used as the PPG signal;
obtaining, from the time frequency spectrum, a noise quality index for the segment; the noise quality index being used to determine whether the segment is corrupted by motion and noise artifacts;
wherein obtaining a noise quality index comprises:
determining a dominant frequency in the time frequency spectrum of the segment;
normalizing the time frequency spectrum to a total power in a narrow band centered at the dominant frequency;
determining a first trace of amplitudes in the narrow band spectrum of the time frequency spectrum centered at the dominant frequency;
determining a second trace of amplitudes in a narrow band spectrum of the time frequency spectrum centered at twice the dominant frequency;
determining a third trace of amplitudes in a narrow band spectrum of the time frequency spectrum centered at three times the dominant frequency;
subtracting the first, second and third traces of amplitudes from the time frequency spectrum;
obtaining, after subtracting, a total power remaining in the time frequency spectrum, said total power remaining referred to as a residual noise power;
determining a difference between the dominant frequency and a heart rate obtained from peak to peak intervals from the signal used as the PPG signal in a time domain, the difference between the dominant frequency and the heart rate obtained from peak to peak intervals referred to as a heart rate frequency difference;
the noise quality index also comprising the heart rate frequency difference; the noise quality index being a weighted sum of factors including the residual noise power and the heart rate frequency difference; weights being selected such that each weighted factor represents less than a predetermined percentage of power in an uncorrupted segment;
applying a statistical learning method, using the noise quality index, to determine whether the segment is corrupted by motion and noise artifacts or not corrupted by motion and noise artifacts;
and,
if motion and noise artifacts are not present, including the segment in determination of a physiological parameter.

9. The computer implemented method of claim 8 wherein the statistical learning method is a Support Vector Machine (SVM).

10. A system for physiological parameter monitoring using a signal used as a Photoplethysmogram (PPG) signal, the system comprising:
a processor configured to:
receive the signal used as the PPG signal;
obtain a time frequency spectrum of a segment of the signal used as the PPG signal;
obtain, from the time frequency spectrum, a noise quality index for the segment; the noise quality index being used to determine whether the segment is corrupted by motion and noise artifacts;
determine a dominant frequency in the time frequency spectrum of the segment;
normalize the time frequency spectrum to the total power in a narrow band centered at the dominant frequency;
determine a first trace of amplitudes in a narrow band spectrum of the time frequency spectrum centered at the dominant frequency;
determine a second trace of amplitudes in a narrow band spectrum of the time frequency spectrum centered at twice the dominant frequency;
determine a third trace of amplitudes in a narrow band spectrum of the time frequency spectrum centered at three times the dominant frequency;
subtract the first, second and third traces of amplitudes from the time frequency spectrum;
obtain, after subtracting, a total power remaining in the time frequency spectrum; the total power remaining referred to as a residual noise power;
determine a difference in frequency between the first trace and the second and third traces; the difference in frequency referred to as a projected difference;
apply a statistical learning method, using the noise quality index, to determine whether the segment is corrupted by motion and noise artifacts or not corrupted by motion and noise artifacts;
and,
if motion and noise artifacts are not present, include the segment in determination of a physiological parameter;
the noise quality index being a weighted sum of factors including the residual noise power and the projected difference; weights being selected such that each weighted factor represents less than a predetermined percentage of power in an uncorrupted segment.

11. The system of claim 10 wherein the statistical learning method is a Support Vector Machine (SVM).

12. The system of claim 10 wherein the processor is further configured to determine a difference between the dominant frequency and a heart rate obtained from peak to peak intervals from the signal used as the PPG signal in a time domain; the difference between the dominant frequency and the heart rate obtained from peak to peak intervals referred to as a heart rate frequency difference; wherein the noise quality index also comprises the heart rate frequency difference; and, wherein the noise quality index is a weighted sum of factors including the residual noise power, the projected difference and the heart rate frequency difference.

13. The system of claim 12 wherein the statistical learning method is a Support Vector Machine (SVM).

14. The system of claim 10 wherein the processor is further configured to preprocess the signal used as the PPG signal before obtaining the time frequency spectrum.

15. The system of claim 14 wherein the processor is configured to preprocess the signal used as the PPG signal by filtering with a bandpass filter of predetermined bandwidth.

16. The system of claim 10 wherein the processor is configured to obtain the time frequency spectrum using variable frequency complex demodulation.

17. A system for detection of motion and noise artifacts in a signal used as a Photoplethysmogram (PPG) signal, the system comprising:
a processor configured to:
receive the signal used as the PPG signal;
obtain a time frequency spectrum of a segment of the signal used as the PPG signal;
obtain, from the time frequency spectrum, a noise quality index for the segment; the noise quality index being used to determine whether the segment is corrupted by motion and noise artifacts;
determine a dominant frequency in the time frequency spectrum of the segment;
normalize the time frequency spectrum to the total power in a narrow band centered at the dominant frequency;
determine a first trace of amplitudes in the narrow band spectrum of the time frequency spectrum centered at the dominant frequency;
determine a second trace of amplitudes in a narrow band spectrum of the time frequency spectrum centered at twice the dominant frequency;
determine a third trace of amplitudes in a narrow band spectrum of the time frequency spectrum centered at three times the dominant frequency;
subtract the first, second and third traces of amplitudes from the time frequency spectrum;
obtain, after subtracting, a total power remaining in the time frequency spectrum; the total power remaining referred to as a residual noise power;
determine a difference between the dominant frequency and a heart rate obtained from peak to peak intervals from the signal used as the PPG signal in a time domain; the difference between the dominant frequency and the heart rate obtained from peak to peak intervals referred to as a heart rate frequency difference;
the noise quality index being a weighted sum of factors including the residual noise power and the heart rate frequency difference; weights being selected such that each weighted factor represents less than a predetermined percentage of power in an uncorrupted segment;
apply a statistical learning method, using the noise quality index, to determine whether the segment is corrupted by motion and noise artifacts or not corrupted by motion and noise artifacts;
and,
if motion and noise artifacts are not present, include the segment in determination of a physiological parameter.

18. The system of claim 17 wherein the statistical learning method is a Support Vector Machine (SVM).

19. A computer program product comprising:
tangible computer usable media, having computer readable code embodied therein, the computer readable code, when executed by one or more processors, causes the one or more processors to:
obtain a time frequency spectrum of a segment of a signal used as a PPG signal;
obtain, from the time frequency spectrum, a noise quality index for the segment; the noise quality index being used to determine whether the segment is corrupted by motion and noise artifacts;
determine a dominant frequency in the time frequency spectrum of the segment;
normalize the time frequency spectrum to the total power in a narrow band centered at the dominant frequency;
determine a first trace of amplitudes in a narrow band spectrum of the time frequency spectrum centered at the dominant frequency;
determine a second trace of amplitudes in a narrow band spectrum of the time frequency spectrum centered at twice the dominant frequency;
determine a third trace of amplitudes in a narrow band spectrum of the time frequency spectrum centered at three times the dominant frequency;
subtract the first, second and third traces of amplitudes from the time frequency spectrum; and
obtain, after subtracting, a total power remaining in the time frequency spectrum; the total power remaining referred to as a residual noise power;
determine a difference in frequency between the first trace and the second and third traces; the difference in frequency referred to as a projected difference;
apply a statistical learning method, using the noise quality index, to determine whether the segment is corrupted by motion and noise artifacts or not corrupted by motion and noise artifacts;
and,
if motion and noise artifacts are not present, include the segment in determination of a physiological parameter;
wherein the noise quality index is a weighted sum of factors including the residual noise power and the projected difference; weights being selected such that each weighted factor represents less than a predetermined percentage of power in an uncorrupted segment.

20. The computer program product of claim 19 wherein the statistical learning method is a Support Vector Machine (SVM).

* * * * *

UNITED STATES PATENT AND TRADEMARK OFFICE
CERTIFICATE OF CORRECTION

PATENT NO. : 10,653,362 B2  
APPLICATION NO. : 15/010345  
DATED : May 19, 2020  
INVENTOR(S) : Ki H Chon et al.

Page 1 of 1

It is certified that error appears in the above-identified patent and that said Letters Patent is hereby corrected as shown below:

On the Title Page

Item (73) should read:  
Assignee: Worcester Polythechnic Institute  
         Worcester, MA Signed and Sealed this  
Thirtieth Day of June, 2020

Andrei Iancu  
*Director of the United States Patent and Trademark Office*